(12) United States Patent
Kato et al.

(10) Patent No.: US 8,673,271 B2
(45) Date of Patent: Mar. 18, 2014

(54) COMPOSITIONS FOR MOUTH CONTAINING AN ANIONIC SURFACTANT HAVING REDUCED ASTRINGENCY

(75) Inventors: Kazuhiko Kato, Tokyo (JP); Manabu Tonomura, Tokyo (JP)

(73) Assignee: Kao Corporation, Tokyo (JP)

( * ) Notice: Subject to any disclaimer, the term of this patent is extended or adjusted under 35 U.S.C. 154(b) by 967 days.

(21) Appl. No.: 10/497,849

(22) PCT Filed: Dec. 20, 2002

(86) PCT No.: PCT/JP02/13356
§ 371 (c)(1),
(2), (4) Date: Jun. 7, 2004

(87) PCT Pub. No.: WO03/055459
PCT Pub. Date: Jul. 10, 2003

(65) Prior Publication Data
US 2005/0042183 A1 Feb. 24, 2005

(30) Foreign Application Priority Data
Dec. 25, 2001 (JP) ................................. 2001-391823

(51) Int. Cl.
*A61Q 11/00* (2006.01)
*A61K 8/02* (2006.01)

(52) U.S. Cl.
USPC ....................................................... 424/49

(58) Field of Classification Search
USPC ....................................................... 424/49
See application file for complete search history.

(56) References Cited

U.S. PATENT DOCUMENTS

| 4,150,151 A | * | 4/1979 | Pader et al. ....................... 424/56 |
| 4,476,107 A | * | 10/1984 | Schmolka ........................ 424/49 |
| 4,550,018 A | * | 10/1985 | Ambike et al. ................... 424/52 |
| 4,725,428 A | * | 2/1988 | Miyahara et al. ................ 424/50 |
| 4,865,839 A | | 9/1989 | Saso |
| 5,108,735 A | * | 4/1992 | Ohtsuki et al. ................... 424/50 |
| 5,328,682 A | * | 7/1994 | Pullen et al. .................... 424/49 |
| 5,372,803 A | | 12/1994 | Williams et al. |
| 5,431,903 A | * | 7/1995 | Majeti et al. .................... 424/52 |
| 5,690,911 A | * | 11/1997 | Mirajkar et al. ................. 424/49 |
| 5,945,088 A | * | 8/1999 | Delli Santi et al. ............. 424/49 |
| 6,013,274 A | * | 1/2000 | Chaykin ........................ 424/440 |
| 6,555,094 B1 | * | 4/2003 | Glandorf et al. ................ 424/52 |
| 6,652,841 B1 | * | 11/2003 | Brown et al. ................... 424/49 |

FOREIGN PATENT DOCUMENTS

| EP | 0 251 542 A2 | | 1/1988 |
| EP | 251542 | | 1/1988 |
| EP | 0 643 957 A2 | | 3/1995 |
| EP | 1 072 253 A1 | | 1/2001 |
| JP | 49-66841 | | 6/1974 |
| JP | 56-113709 | | 9/1981 |
| JP | 63-8324 | | 1/1988 |
| JP | 63-8326 | | 1/1988 |
| JP | 2-292210 | | 12/1990 |
| JP | 4-139117 | | 5/1992 |
| JP | 5-97639 | | 4/1993 |
| JP | 8-325126 | | 12/1996 |
| JP | 10-139643 | | 5/1998 |
| JP | 11-71253 | | 3/1999 |
| JP | 11-116451 | | 4/1999 |
| JP | 2000-26256 | | 1/2000 |
| JP | 2000-247852 | | 9/2000 |
| JP | 2000-302655 | | 10/2000 |
| JP | 2001-55318 | | 2/2001 |
| JP | 2002-20251 | | 1/2002 |
| JP | 2002-265340 | | 9/2002 |
| WO | WO 91/11987 | | 8/1991 |
| WO | WO 93/04664 | | 3/1993 |
| WO | WO 95/01155 | * | 1/1995 |

* cited by examiner

*Primary Examiner* — Lezah Roberts
(74) *Attorney, Agent, or Firm* — Oblon, Spivak, McClelland, Maier & Neustadt, L.L.P.

(57) ABSTRACT

The present invention relates to an oral care composition, which contains the following components (A), (B) and (C):
(A) an inorganic acid and/or an organic acid,
(B) an anionic surfactant,
(C) at least one compound selected from polyglycerin fatty acid esters, sorbitan fatty acid esters, polyoxyethylene higher alcohol ethers having from 6 to 14 carbon atoms, polyoxyethylene fatty acid esters and polyoxyethylene polyoxypropylene copolymers. The oral care composition according to the present invention is significantly excellent in reducing astringency and bitterness inherent in anionic surfactants.

11 Claims, No Drawings

COMPOSITIONS FOR MOUTH CONTAINING AN ANIONIC SURFACTANT HAVING REDUCED ASTRINGENCY

TECHNICAL FIELD

The present invention relates to an oral care composition which contains a nonionic surfactant in addition to a composition containing an inorganic and/or organic acid and an anionic surfactant, thereby reducing the astringency or bitterness inherent in the anionic surfactant.

BACKGROUND ART

A variety of anionic surfactants have conventionally been used as a foaming agent to be added to an oral care composition such as toothpaste and liquid dentifrice. It is however known that anionic surfactants tend to be bound to the mucous membrane in the mouth and consequently cause astringency or bitterness in the mouth even after rinsing with water. Intensity of this astringency or bitterness correlates with the amount of the anionic surfactants bound to the mucous membrane in the mouth and astringency or bitterness can be reduced by lowering the amount of the anionic surfactants bound to the mucous membrane in the mouth.

Methods for reducing such astringency or bitterness attributable to anionic surfactants are described in the following documents. Japanese Patent Publication No. Sho 52-24573 discloses a method of using sodium lauryl sulfate in combination with an alkyl diethanolamide and carrageenan. Japanese Patent Publication No. Sho 62-17563 proposes a method of using sodium alkyl sulfate in combination with an N-(long chain acyl)amino acid salt and a nonionic surfactant.

The amount of the anionic surfactant which binds to the mucous membrane in the mouth varies depending on the pH of the oral care composition containing it. Particularly when an oral care composition has an acidic pH, the amount which binds to the mucous membrane in the mouth becomes considerably higher than that of a composition having an alkaline pH, leading to a strongly perceivable astringency or bitterness in the mouth even after rinsing with water.

The above-described methods as proposed previously do not take into account the influence of the pH of an oral care composition on the amount of the anionic surfactant which binds to the mucous membrane in the mouth, so that when the oral care composition has a neutral or acidic pH, the incorporation therein of additional components as described in the publications is not sufficient for reducing the astringency or bitterness caused by the use of a composition having a neutral or an acidic pH.

An object of the present invention is to provide an acid composition for oral care which does not taste astringent or bitter and has excellent feeling upon use.

DISCLOSURE OF THE INVENTION

The present inventors succeeded in obtaining an oral care composition which leaves neither astringency nor bitterness in the mouth and has excellent feeling upon use, which contains in combination with a composition containing an inorganic acid and/or an organic acid and an anionic surfactant, at least one compound selected from polyglycerin fatty acid esters, sorbitan fatty acid esters, polyoxyethylene higher alcohol ethers, polyoxyethylene fatty acid esters and polyoxyethylene polyoxypropylene copolymers.

In the present invention, there is thus provided an oral care composition containing the following components (A), (B) and (C):
(A) an inorganic acid and/or an organic acid,
(B) an anionic surfactant,
(C) at least one compound selected from polyglycerin fatty acid esters, sorbitan fatty acid esters, polyoxyethylene higher alcohol ethers having from 6 to 14 carbon atoms, polyoxyethylene fatty acid esters and polyoxyethylene polyoxypropylene copolymers.

BEST MODE FOR CARRYING OUT THE INVENTION

As Component (A) to be used in the present invention, an inorganic acid and an organic acid can be used either singly or in combination. Examples of the inorganic acid include hydrochloric acid, sulfuric acid and phosphoric acid, while those of the organic acid include monobasic acids such as formic acid, acetic acid and propionic acid; dibasic acids such as oxalic acid, succinic acid, fumaric acid, adipic acid and maleic acid; hydroxycarboxylic acids such as lactic acid, glycolic acid, tartaric acid, malic acid, citric acid, ascorbic acid, gluconic acid and glyceric acid, acidic amino acids such as glutamic acid and aspartic acid, keto acids such as pyruvic acid, acetoacetic acid and revulinic acid, and aromatic carboxylic acids such as benzoic acid and salicylic acid. of these, any one of lactic acid, acetic acid, citric acid, malic acid, succinic acid, tartaric acid and adipic acid is preferred, with lactic acid, citric acid and malic acid being more preferred.

In the oral care composition according to the present invention, two or more of the above-described acids may be used in combination as Component (A). Component (A) is preferably contained in an amount of from 0.1 to 30 mass %, especially preferably from 0.5 to 15 mass %, in the composition of the present invention.

Examples of the anionic surfactant to be used as Component (B) in the present invention include acylamino acid salts such as sodium acylglutamate and sodium acyl sarcosinate, alkyl phosphates such as sodium alkylphosphates, alkyl sulfates, sulfonated monoglycerides of higher fatty acids, fatty acid esters of isethionic acid. The alkyl or acyl group of the hydrophobic group has preferably from 6 to 18, more preferably from 10 to 14 carbon atoms. Sodium salts are also preferred.

As Component (B), alkyl sulfates are more preferred because they have good foaming and are available at low cost.

Component (B) is preferably added in an amount of from 0.1 to 5 mass %, more preferably from 0.2 to 2 mass % in the composition of the present invention.

Examples of the nonionic surfactant to be used as Component (C) in the present invention include polyglycerin fatty acid esters, sorbitan fatty acid esters, polyoxyethylene higher alcohol ethers having from 6 to 14 carbon atoms, polyoxyethylene fatty acid esters and polyoxyethylene polyoxypropylene copolymers.

Examples of the polyglycerin fatty acid esters include those obtained by esterification of a polyglycerin having an average polymerization degree of from 2 to 30 and a fatty acid having from 8 to 24 carbon atoms. From the viewpoints of the reducing effects on astringency or bitterness, foaming property and tastiness, a monoester consisting of a polyglycerin having an average polymerization degree of from 4 to 12 and a fatty acid having from 12 to 18 carbon atoms is preferred. As monoesters, those having an average esterification degree not greater than 1.4 are used and among others, from 0.8 to 1.3 are preferred.

Preferred examples of the polyglycerin fatty acid esters include hexaglycerin monomyristate, decaglycerin monomyristate, hexaglycerin monolaurate, decaglycerin monolaurate, hexaglycerin monostearate and decaglycerin monooleate.

Examples of the sorbitan fatty acid esters include those obtained by esterification of a sorbitan and a fatty acid having from 8 to 24 carbon atoms. From the viewpoints of the reducing effects on astringency or bitterness, foaming property and tastiness, a monoester consisting of a polyglycerin having an average polymerization degree of from 4 to 12 and a fatty acid having from 12 to 18 carbon atoms is preferred. As monoesters, those having an average esterification degree not greater than 3.0 are used and among others, from 0.8 to 2.0 are preferred.

Examples of the polyoxyethylene higher alcohol ethers include those obtained by etherification of polyoxyethylene with a higher alcohol having from 6 to 14 carbon atoms. From the viewpoints of the reducing effects on astringency or bitterness, foaming property and tastiness, an ether consisting of polyoxyethylene having an average polymerization degree of from 5 to 100 and a higher alcohol having from 10 to 14 carbon atoms is preferred.

Examples of the polyoxyethylene fatty acid esters include those obtained by esterification of polyoxyethylene and a fatty acid having from 6 to 14 carbon atoms. From the viewpoints of the reducing effects on astringency or bitterness, foaming property and tastiness, esters consisting of polyoxyethylene having an average polymerization degree of from 5 to 100 and a fatty acid having from 10 to 14 carbon atoms are preferred.

Examples of the polyoxyethylene polyoxypropylene copolymers include those obtained by binding of polyoxypropylene to polyoxyethylene. From the viewpoints of the reducing effects on astringency, foaming property and tastiness, a copolymer consisting of a polyoxypropylene having an average polymerization degree of from 10 to 50 and a polyoxyethylene having an average polymerization degree of from 20 to 100 is preferred.

Component (C) is preferably added in an amount of from 0.1 to 20 mass %, more preferably from 1 to 10 mass % in the oral care composition according to the present invention.

The concentration of the composition, under which pH is measured, may be selected depending on the practical use of the composition. For example, when the composition is used as a toothpaste, the pH is measured on the assumption of the practical concentration of the composition being 30 mass % in its aqueous solution. When the composition is used as a mouthwash, the pH of the composition is measured without dilution. The oral care composition according to the present invention preferably has a pH of from 3 to 5.5.

The oral care composition according to the present invention contains components ordinarily employed for such compositions, in addition to the above-described components. Examples thereof include water, foaming aid, enzyme, abrasive, humectant, sweetener, preservative, bactericide, medicinal component, pH regulator, binder, pigment, colorant and flavor.

Examples of the abrasive include silica abrasives such as precipitated silica, silica gel, aluminosilicate, zirconosilicate, calcium secondary phosphate•dihydrate and nonhydrate, calcium pyrophosphate, calcium carbonate, alumina, aluminum hydroxide, magnesium acetate, magnesium tertiary phosphate, zeolite and synthetic resin abrasives.

Examples of the binder include cellulose derivatives such as sodium carboxymethylcellulose, methyl cellulose, hydroxyethyl cellulose, and sodium carboxymethylhydroxyethyl cellulose, alginate esters such as sodium alginate and propylene glycol alginate, gums such as carrageenan, xanthan gum, tragacanth gum, guar gum and gum Arabic, synthetic binders such as polyvinyl alcohol, sodium polyacrylate and polyvinylpyrrolidone, and inorganic binders such as aluminum silica gel and laponite.

Preferred examples of the humectant include glycerin, sorbitol, propylene glycol, polyethylene glycol, xylitol, maltitol, lactitol and trehalose.

Examples of the sweetener include saccharin sodium, stevioside, stevia extract, p-methoxy cinnamic aldehyde, neohesperidin dihydrochalcone, and perillartine.

Examples of the flavor include l-menthol, carvone, anethole, eugenol, limonene, peppermint oil, spearmint oil, ocimene, n-amyl alcohol, citronellol, α-terpineol, methyl salicylate, methyl acetate, citronellyl acetate, cineol, linalool, ethyl linalool, vanillin, thymol, lemon oil, orange oil, sage oil, rosemary oil, cinnamon oil, pimiento oil, perilla oil, clove oil and eucalyptus oil.

Examples of various effective ingredients include fluorides such as sodium fluoride, potassium fluoride, ammonium fluoride, stannous fluoride and sodium monofluorophosphate; water soluble phosphoric acid compounds such as potassium salts or sodium salts of orthophosphoric acid; aluminum chlorohydroxy allantoinate, hinokitiol, lysozyme chloride, glycyrrhizinic acid and salts thereof, sodium chloride, tranexamic acid, epsilon-aminocaproic acid, dl-tocopherol acetate, azulene, glycyrrhetinic acid, copper compounds such as sodium copper chlorophyllin and copper gluconate, aluminum lactate, strontium chloride, potassium nitrate, berberine, hydroxamic acid and derivatives thereof, sodium tripolyphosphate, zeolite, dextranase, mutanase, amylase, methoxyethylene, maleic anhydride copolymer, polyvinylpyrrolidone, epidihydrocholesterin, dihydrocholesterol, zinc citrate, extracts of Japanese Angelica root, *Phellodendri* cortex, clove, rosemary, *Scutellaria* root and safflower, alpha-bisabolol, chlorhexidine salts, cetylpyridinium chloride, benzethonium chloride and trichlorocarbanilide.

The oral care compositions according to the present invention include toothpaste, liquid dentifrice, and mouthwash.

EXAMPLES

Example 1

A toothpaste composed of the components as shown in Table 1 was prepared.

Bitterness and astringency were organoleptically evaluated after the use of the toothpaste.
(Evaluation Method)

Ten volunteers (5 males and 5 females) applied 1 g of each of the toothpastes on their toothbrushes used in routinely, brushed their teeth freely for about 2 minutes, and rinsed their mouth with tap water. This tooth brushing was conducted three times a day for 3 consecutive days. During this period, the volunteers were asked how strong bitterness or astringency was felt after brushing and rinsing of their teeth, and their responses were evaluated in accordance with the following criteria: Bitterness (or astringency) after rinsing

| | |
|---|---|
| Very strong bitterness or astringency remained: | D |
| A little bitterness or astringency remained: | C |
| Bitterness or astringency hardly remained: | B |
| Neither bitterness nor astringency remained: | A |

The comprehensive evaluation was determined by taking the largest number of volunteers sharing the same criterion in common.

TABLE 1

Toothpaste

| Component (mass %) | Example 1 | Example 2 | Example 3 | Example 4 | Example 5 | Example 6 | Example 7 | Comparative Example 1 | Comparative Example 2 | Comparative Example 3 | Comparative Example 4 | Comparative Example 5 |
|---|---|---|---|---|---|---|---|---|---|---|---|---|
| DL-malic acid | 2 | | | 1 | | | | | | 2 | | |
| Citric acid | | 2 | | | | 1 | 1 | 2 | | | | 2 |
| Lactic acid | | | 3 | | | | 1 | | 3 | | | |
| Phosphoric acid | | | | 0.5 | 1.5 | 0.5 | | | | | 1.5 | |
| Sodium lauryl sulfate | 1.5 | | | 1.5 | 1.5 | 1.5 | 1.5 | 1.5 | 0.3 | 0.3 | 0.3 | 1.5 |
| Sodium lauroyl glutamate | | 1.5 | | | | | | | | | | |
| Sodium lauryl phosphate | | | 1.5 | | | | | | | | | |
| Hexaglyceryl monomyristate | 3 | | | | 2 | | 2 | | | | | |
| Sorbitan monolaurate | | 5 | | | | | | | | | | |
| Polyoxyethylene (20) myristyl alcohol ether | | | 3 | | 1 | | | | | | | |
| Polyoxyethylene (40) laurate ester | | | | | | 4 | | | | | | |
| Polyoxyethylene (80) polyoxypropylene (20) copolymer | | | | 10 | | | 5 | | | | | |
| Myristyl diethanolamide | | | | | | | | | | | | 1 |
| N-lauroylsarcosine sodium | | | | | | | | | 0.5 | 0.5 | 0.5 | |
| Sucrose fatty acid ester | | | | | | | | | 2.0 | | | |
| Polyoxyethylene (40) stearyl alcohol ester | | | | | | | | | | 2.0 | | |
| Polyoxyethylene (40) monostearate ester | | | | | | | | | | | 2.0 | |
| Sorbitol solution | 30 | 30 | 30 | 30 | 30 | 30 | 30 | 30 | 30 | 30 | 30 | 30 |
| Propylene glycol | 5 | 5 | 5 | 5 | 5 | 5 | 5 | 5 | 5 | 5 | 5 | 5 |
| Saccharin sodium | 0.1 | 0.1 | 0.1 | 0.1 | 0.1 | 0.1 | 0.1 | 0.1 | 0.1 | 0.1 | 0.1 | 0.1 |
| Sodium carboxymethylcellulose | 1.5 | 1.5 | 1.5 | 1.5 | 1.5 | 15 | 1.5 | | 1.5 | 1.5 | 1.5 | 1.5 |
| Carrageenan | | | | | | | | 1 | | | | |
| Sodium fluoride | 0.21 | 0.21 | 0.21 | 0.21 | 0.21 | 0.21 | 0.21 | 0.21 | 0.21 | 0.21 | 0.21 | 0.21 |
| Thickening silica | 5 | 5 | 5 | 5 | 5 | 5 | 5 | 5 | 5 | 5 | 5 | 5 |
| Abrasive silica | 15 | 15 | 15 | 15 | 15 | 15 | 15 | 15 | 15 | 15 | 15 | 15 |
| Flavor | 1 | 1 | 1 | 1 | 1 | 1 | 1 | 1 | 1 | 1 | 1 | 1 |
| Purified water | q.s. | q.s. | q.s. | q.s. | q.s. | q.s. | q.s. | q.s. | q.s. | q.s. | q.s. | q.s. |
| pH regulator | q.s. | q.s. | q.s. | q.s. | q.s. | q.s. | q.s. | q.s. | q.s. | q.s. | q.s. | q.s. |
| Total | 100.0 | 100.0 | 100.0 | 100.0 | 100.0 | 100.0 | 100.0 | 100.0 | 100.0 | 100.0 | 100.0 | 100.0 |
| pH | 5.0 | 5.0 | 5.0 | 4.5 | 4.5 | 5.0 | 4.0 | 4.5 | 4.0 | 4.5 | 5.0 | 5.0 |
| Evaluation of taste | A | B | B | B | A | B | A | D | D | D | D | D |

Bitterness and astringency were hardly felt when the toothpastes of Examples 1 to 7 containing a nonionic surfactant as Component (C) were used. In particular, neither bitterness nor astringency was felt when the toothpastes of Examples 1, 5 and 7 containing a polyglycerin fatty acid ester singly or in combination with another nonionic surfactant were used. By contrast, both bitterness and astringency were strongly felt when the toothpaste of Comparative Example 1 free of a nonionic surfactant was used. Although the toothpastes of Comparative Examples 2 to 4 contained an N-(long chain) acylamino acid and nonionic surfactant, i.e., the taste modifying components of the oral care composition as described in Japanese Patent Publication No. Sho 62-17563, both bitterness and astringency were strongly felt in the mouth. The toothpaste of Comparative Example 5 contained, in addition to sodium lauryl sulfate (anionic surfactant), lauryl diethanolamide and carrageenan i.e., the taste modifying components for the oral care composition as described in Japanese Patent Publication No. Sho 52-24573, but both bitterness and astringency were strongly felt in the mouth.

TABLE 2

Liquid dentifrice

| Component (mass %) | Example 1 | Example 2 | Example 3 | Example 4 | Example 5 | Example 6 | Example 7 | Comparative Example 1 | Comparative Example 2 | Comparative Example 3 | Comparative Example 4 | Comparative Example 5 |
|---|---|---|---|---|---|---|---|---|---|---|---|---|
| DL-malic acid | 2 | | | 1 | | | | | | 2 | | |
| Citric acid | | 2 | | | | 1 | 1 | 2 | | | | 2 |
| Lactic acid | | | 3 | | | | 1 | | 3 | | | |
| Phosphoric acid | | | | 0.5 | 1.5 | 0.5 | | | | | 1.5 | |
| Sodium lauryl sulfate | 1.5 | | | 1.5 | 1.5 | 1.5 | 1.5 | 1.5 | 0.3 | 0.3 | 0.3 | 1.5 |
| Sodium lauroyl glutamate | | 1.5 | | | | | | | | | | |
| Sodium lauryl phosphate | | | 1.5 | | | | | | | | | |
| Hexaglyceryl monomyristate | 3 | | | | 2 | | 2 | | | | | |
| Sorbitan monolaurate | | 5 | | | | | | | | | | |
| Polyoxyethylene (20) myristyl alcohol ether | | | 3 | | 1 | | | | | | | |
| Polyoxyethylene (40) laurate ester | | | | | | 4 | | | | | | |

TABLE 2-continued

| | Liquid dentifrice | | | | | | | | | | | |
|---|---|---|---|---|---|---|---|---|---|---|---|---|
| | Example | | | | | | | Comparative Example | | | | |
| Component (mass %) | 1 | 2 | 3 | 4 | 5 | 6 | 7 | 1 | 2 | 3 | 4 | 5 |
| Polyoxyethylene (80) polyoxypropylene (20) copolymer | | | | 10 | | | 5 | | | | | |
| Myristyl diethanolamide | | | | | | | | | | | | 1 |
| N-lauroylsarcosine sodium | | | | | | | | | 0.5 | 0.5 | 0.5 | |
| Sucrose fatty acid ester | | | | | | | | | 2.0 | | | |
| Polyoxyethylene (40) stearyl alcohol ester | | | | | | | | | | 2.0 | | |
| Polyoxyethylene (40) monostearate ester | | | | | | | | | | | 2.0 | |
| Sorbitol solution | 30 | 30 | 30 | 30 | 30 | 30 | 30 | 30 | 30 | 30 | 30 | 30 |
| Propylene glycol | 5 | 5 | 5 | 5 | 5 | 5 | 5 | 5 | 5 | 5 | 5 | 5 |
| Saccharin sodium | 0.1 | 0.1 | 0.1 | 0.1 | 0.1 | 0.1 | 0.1 | 0.1 | 0.1 | 0.1 | 0.1 | 0.1 |
| Sodium carboxymethylcellulose | 0.8 | 0.8 | 0.8 | 0.8 | 0.8 | 0.8 | 0.8 | | 0.8 | 0.8 | 0.8 | 0.8 |
| Carrageenan | | | | | | | | 1 | | | | |
| Sodium fluoride | 0.21 | 0.21 | 0.21 | 0.21 | 0.21 | 0.21 | 0.21 | 0.21 | 0.21 | 0.21 | 0.21 | 0.21 |
| Thickening silica | 2 | 2 | 2 | 2 | 2 | 2 | 2 | 2 | 2 | 2 | 2 | 2 |
| Abrasive silica | 15 | 15 | 15 | 15 | 15 | 15 | 15 | 15 | 15 | 15 | 15 | 15 |
| Flavor | 1 | 1 | 1 | 1 | 1 | 1 | 1 | 1 | 1 | 1 | 1 | 1 |
| Purified water | q.s. | q.s. | q.s. | q.s. | q.s. | q.s. | q.s. | q.s. | q.s. | q.s. | q.s. | q.s. |
| pH regulator | q.s. | q.s. | q.s. | q.s. | q.s. | q.s. | q.s. | q.s. | q.s. | q.s. | q.s. | q.s. |
| Total | 100.0 | 100.0 | 100.0 | 100.0 | 100.0 | 100.0 | 100.0 | 100.0 | 100.0 | 100.0 | 100.0 | 100.0 |
| pH | 5.0 | 5.0 | 5.0 | 4.5 | 4.5 | 5.0 | 4.0 | 4.5 | 4.0 | 4.5 | 5.0 | 5.0 |
| Evaluation of taste | A | B | B | B | A | B | A | D | D | D | D | D |

Bitterness and astringency were hardly felt when the liquid dentifrices of Examples 8 to 14 containing a nonionic surfactant as Component (C) were used. In particular, neither bitterness nor astringency was felt when the liquid dentifrices of Examples 8, 10 and 14 containing a polyglycerin fatty acid ester singly or in combination with another nonionic surfactant were used. By contrast, both bitterness and astringency were strongly felt when the liquid dentifrice of Comparative Example 6 free of a nonionic surfactant was used. Although the liquid dentifrices of Comparative Examples 7 to 9 contained an N-(long chain)acylamino acid and nonionic surfactant, i.e., the taste modifying components of the oral care composition as described in Japanese Patent Publication No. Sho 62-17563, both bitterness and astringency were strongly felt in the mouth. The liquid dentifrice of Comparative Example 10 contained, in addition to sodium lauryl sulfate (anionic surfactant), lauryl diethanolamide and carrageenan, i.e., taste modifying components for the oral care composition as described in Japanese Patent Publication No. Sho 52-24573, but both bitterness and astringency were strongly felt in the mouth.

INDUSTRIAL APPLICABILITY

The oral care compositions according to the present invention have excellent feeling upon use without leaving astringency and bitterness in the mouth even after rinsing with water. These advantages were attained by incorporating, in a composition containing an inorganic acid and/or an organic acid and an anionic surfactant, at least one compound selected from polyglycerin fatty acid esters, sorbitan fatty acid esters, polyoxyethylene higher alcohol ethers having from 6 to 14 carbon atoms, polyoxyethylene fatty acid esters and polyoxyethylene polyoxypropylene copolymer.

The invention claimed is:

1. An oral care composition, comprising the following components (A), (B) and (C):
    (A) 0.5 to 15 wt. % of an acid which is at least one selected from the group consisting of phosphoric acid, lactic acid, citric acid and malic acid,
    (B) 0.1 to 5 wt. % of an alkyl sulfate; and
    (C) 0.1 to 10 wt. % of an ester consisting of polyglycerin having an average polymerization degree of from 4 to 12 and a fatty acid having from 12 to 18 carbon atoms,
wherein the oral care composition has a pH of from 4.0 to 5.0; and
    wherein component (B) and component (C) are present in a ratio of from 1.5:3 to 1.5:5.

2. The oral care composition of claim 1, wherein component (B) is present in an amount of 0.2 to 2 wt. %.

3. The oral care composition of claim 1, further comprising at least one element selected from the group consisting of water, a foaming aid, an enzyme, an abrasive, a humectant, a sweetener, a preservative, a bactericide, a medicinal component, a pH regulator, a binder, a pigment, a colorant and a flavor.

4. The oral care composition of claim 3, wherein said composition comprises an abrasive selected from the group consisting of precipitated silica, silica gel, aluminosilicate, zirconosilicate, calcium secondary phosphate dehydrate, calcium secondary phosphate nonhydrate, calcium pyrophosphate, calcium carbonate, alumina, aluminum hydroxide, magnesium acetate, magnesium tertiary phosphate, zeolite, synthetic resin abrasives and a mixture thereof.

5. The oral care composition of claim 3, wherein said composition comprises a binder selected from the group consisting of sodium carboxymethylcellulose, methyl cellulose, hydroxyethyl cellulose, sodium carboxymethylhydroxyethyl cellulose, sodium alginate, propylene glycol alginate, carrageenan, xanthan gum, tragacanth gum, guar gum, gum Arabic, polyvinyl alcohol, sodium polyacrylate, polyvinylpyrrolidone, aluminum silica gel, laponite and a mixture thereof.

6. The oral care composition of claim 3, wherein said composition comprises a humectant selected from the group consisting of glycerin, sorbitol, propylene glycol, polyethylene glycol, xylitol, maltitol, lactitol, trehalose and a mixture thereof.

7. The oral care composition of claim 3, wherein said composition comprises a sweetener selected from the group consisting of saccharin sodium, stevioside, stevia extract, p-methoxy cinnamic aldehyde, neohesperidin dihydrochalcone, perillartine and a mixture thereof.

8. The oral care composition of claim 3, wherein said composition comprises a flavor selected from the group consisting of l-menthol, carvone, anethole, eugenol, limonene, peppermint oil, spearmint oil, ocimene, n-amyl alcohol, citronellol, α-terpineol, methyl salicylate, methyl acetate, citronellyl acetate, cineol, linalool, ethyl linalool, vanillin, thymol, lemon oil, orange oil, sage oil, rosemary oil, cinnamon oil, pimiento oil, perilla oil, clove oil, eucalyptus oil and a mixture thereof.

9. The oral care composition of claim 1, wherein said composition further comprises an element selected from the group consisting of sodium fluoride, potassium fluoride, ammonium fluoride, stannous fluoride, sodium monofluorophosphate; potassium salts or sodium salts of orthophosphoric acid; aluminum chlorohydroxy allantoinate, hinokitiol, lysozyme chloride, glycyrrhizinic acid and salts thereof, sodium chloride, tranexamic acid, ε-aminocaproic acid, dl-tocopherol acetate, azulene, glycyrrhetinic acid, sodium copper chlorophyllin, copper gluconate, aluminum lactate, strontium chloride, potassium nitrate, berberine, hydroxamic acid and derivatives thereof, sodium tripolyphosphate, zeolite, dextranase, mutanase, amylase, methoxyethylene, maleic anhydride copolymer, polyvinylpyrrolidone, epidihydrocholesterin, dihydrocholesterol, zinc citrate, extracts of Japanese Angelica root, *Phellodendri* cortex, clove, rosemary, *Scutellaria* root and safflower, α-bisabolol, chlorhexidine salts, cetylpyridinium chloride, benzethonium chloride, trichlorocarbanilide and a mixture thereof.

10. The oral care composition according to claim 1, wherein said pH is from 4.5 to 5.0.

11. The oral care composition according to claim 1, wherein component (B) further comprises an acylglutamate.

* * * * *